United States Patent [19]

Benecke et al.

[11] 4,440,781

[45] Apr. 3, 1984

[54] OXYOCTADECANOATES AS PSYCHOTROPIC AGENTS

[75] Inventors: Herman P. Benecke; Bob E. Sherwood, both of Columbus, Ohio

[73] Assignee: The Vinoxen Company, Inc., Stamford, Conn.

[21] Appl. No.: 387,636

[22] Filed: Jun. 11, 1982

[51] Int. Cl.³ .................... A61K 31/34; C07D 307/12; C07D 307/32; C07D 307/28
[52] U.S. Cl. ................. 424/285; 424/248.55; 424/267; 424/274; 544/152; 546/214; 548/517; 549/473; 549/475; 549/488; 549/496; 549/501
[58] Field of Search .............. 549/473, 475, 488, 496, 549/501; 424/285, 248.55, 267, 274; 544/152; 546/214; 548/517

[56] References Cited

U.S. PATENT DOCUMENTS

| | | | |
|---|---|---|---|
| 3,954,813 | 5/1976 | Nedenskov et al. | 549/501 |
| 4,009,187 | 2/1977 | Eliasson et al. | 549/501 X |
| 4,048,198 | 9/1977 | Nedenskov et al. | 549/488 |

OTHER PUBLICATIONS

Abott et al., Chemical Abstracts, vol. 76 (1972) 336876.

*Primary Examiner*—Richard Raymond
*Attorney, Agent, or Firm*—Millen & White

[57] ABSTRACT

A method for producing a psychotropic response, especially for alleviating the symptoms of alcohol withdrawal, comprises administering to a human or animal subject in need thereof a psychotropically effective non-toxic amount of an oxyoctadecanoate. A composition for use in the present method is provided.

19 Claims, No Drawings

OXYOCTADECANOATES AS PSYCHOTROPIC AGENTS

BACKGROUND OF THE INVENTION

This invention relates to a method for producing a psychotropic response involving administration of an oxyoctadecanoate. In a composition of matter aspect, the invention also relates to a pharmaceutical composition suitable for use with the foregoing method.

Several methyl 9,12- and 10,13-oxyoctadecanoates are described in the literature. See, e.g., Abbot et al., Chem. Phys. Lipids, 4, 351 (1970); Ibid., 7, 279 (1971); Ibid., 7, 290 (1971); and Gunstone et al., Ibid., 10, 89 (1973). These references do not disclose physiological activity for the described compounds.

Other furanoid acids having physiological but not psychotropic activity are known, e.g., the prostaglandin analogs of U.S. Pat. Nos. 3,883,659, 4,048,198, 4,088,779 and the hypolipidemic agents of U.S. Pat. No. 4,244,958. Structurally more remote furanoid compounds having physiological and/or psychotropic activity include the tetrahydrofuranyl-isobutyrate spasmolytics and vasodilators of U.S. Pat. No. 4,139,631; the carbamoyloxy tetrahydrofuran oral hypnotics of U.S. Pat. No. 3,331,861; the ethyl (β-N-methylfurfurylamino)propionate tranquilizer of U.S. Pat. No. 3,760,086; and the 5-(substituted)phenylfurfuryl alcohol anti-inflammatory agents of U.S. Pat. No. 3,931,247.

OBJECTS OF THE INVENTION

One object of the present invention is to provide a method for producing a psychotropic response, particularly at least one of an antidepressant, tranquilizing or anticonvulsant response, or alleviation of the symptoms of alcohol intoxication or alcohol or tobacco withdrawal.

Another object of the present invention is to provide a pharmaceutical composition for use in the foregoing method.

Upon further study of the specification and appended claims, further objects and advantages of this invention will become apparent to those skilled in the art.

SUMMARY OF THE INVENTION

In a method aspect, the present invention provides a method for producing a psychotropic response in a human or animal subject, comprising administering to said subject a psychotropically effective non-toxic amount of a 9,12-oxyoctadecanoate having the formula I

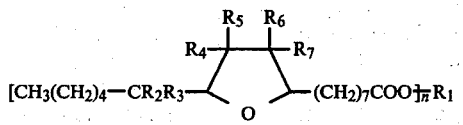

wherein $n=1$ and $R_1$ is H, lower alkyl, cyclo(lower)alkyl, aryl(lower)alkyl, lower alkoxy(lower)alkyl, di(lower)alkylamino(lower)alkyl, cyclic amino(lower)alkyl or alkanoylamino(lower)alkyl; or $n=2-6$ and $R_1$ is a lower alkyl or cyclo(lower)alkyl polyol residue; and (a) $R_2$, $R_3$, $R_4$, $R_5$ and $R_6$ are each H; and $R_7$ is OH; or (b) $R_2$, $R_3$, $R_4$ and $R_5$ are each H; and $R_6$ and $R_7$ together are O; or (c) $R_2$, $R_3$, $R_4$, $R_6$ and $R_7$ are each H; and $R_5$ is OH; or (d) $R_2$, $R_3$, $R_6$ and $R_7$ are each H; and $R_4$ and $R_5$ together are O; or (e) $R_2$ is OH; and $R_3$, $R_4$, $R_5$, $R_6$ and $R_7$ are each H; or (f) $R_2$ is OH; $R_3$, $R_4$ and $R_6$ are each H; and $R_5$ and $R_7$ together are a C—C bond; or (g) $R_2$ and $R_3$ together are O; and $R_4$, $R_5$, $R_6$ and $R_7$ are each H; or (h) $R_2$ and $R_3$ together are O; $R_4$ and $R_6$ are each H; and $R_5$ and $R_7$ together are a C—C bond; or a 10,13-oxyoctadecanoate having the formula II

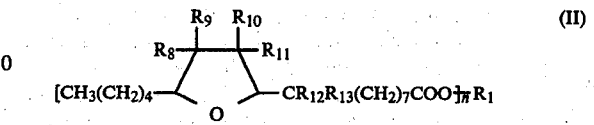

wherein n and $R_1$ are as defined hereinabove; and (a) $R_8$, $R_9$, $R_{10}$, $R_{11}$ and $R_{12}$ are each H; and $R_{13}$ is OH; or (b) $R_8$, $R_9$, $R_{10}$ and $R_{11}$ are each H; and $R_{12}$ and $R_{13}$ together are O; or (c) $R_8$, $R_{10}$ and $R_{12}$ are each H; $R_9$ and $R_{11}$ together are a C—C bond; and $R_{13}$ is OH; or (d) $R_8$ and $R_{10}$ are each H; $R_9$ and $R_{11}$ together are a C—C bond; and $R_{12}$ and $R_{13}$ together are O; or (e) $R_8$, $R_9$, $R_{10}$, $R_{12}$ and $R_{13}$ are each H; and $R_{11}$ is OH; or (f) $R_8$, $R_9$, $R_{12}$ and $R_{13}$ are each H; and $R_{10}$ and $R_{11}$ together are O; or (g) $R_8$ is OH; and $R_9$, $R_{10}$, $R_{11}$, $R_{12}$, and $R_{13}$ are each H; or (h) $R_8$ and $R_9$ together are O; and $R_{10}$, $R_{11}$, $R_{12}$ and $R_{13}$ are each H, or a pharmaceutically acceptable addition salt thereof.

In a composition aspect, the present invention provides a psychotropic composition comprising a non-toxic amount effective for producing a psychotropic response in a human or animal subject of an oxyoctadecanoate, and a pharmaceutically acceptable carrier, as well as novel oxyoctadecanoates.

DETAILED DISCUSSION

The term "oxyoctadecanoate" as used herein embraces the acids and/or esters of formulae I and II, and pharmaceutically acceptable addition salts thereof.

Suitable esters can have the formulae I and II, wherein $n=1$, and $R_1$ is lower alkyl, cyclo(lower)alkyl, aryl(lower)alkyl, lower alkoxy(lower)alkyl, di(lower)alkylamino(lower)alkyl, cyclic amino(lower)alkyl, alkanoylamino(lower)alkyl, and the like.

Illustrative lower alkyl esters include straight or branched chain $C_{1-6}$ alkyl esters, e.g., methyl, ethyl, propyl, isopropyl, tert-butyl, pentyl, hexyl and the like, preferably methyl or ethyl.

Illustrative cyclo(lower)alkyl esters include $C_{3-6}$ cycloalkylesters, e.g., cyclopropyl, cyclobutyl, cyclopentyl, cyclohexyl and the like.

Illustrative aryl(lower)alkyl esters include phenyl-$C_{1-6}$ alkyl esters, e.g., benzyl, phenylethyl and the like; substituted phenyl-$C_{1-6}$ alkyl esters, e.g. p-tolylmethyl, m-chlorophenethyl, and the like; and heteroaromatic-substituted $C_{1-6}$ alkyl esters, e.g., pyridylmethyl and the like.

Illustrative lower alkoxy(lower)alkyl esters include $C_{1-6}$ alkoxy-substituted $C_{1-6}$ alkyl esters, e.g., methoxymethyl, methoxypropyl, ethoxyethyl and the like.

Illustrative di(lower)alkylamino(lower)alkyl esters include, e.g., dimethylaminoethyl, diethylaminoethyl and the like.

Illustrative cyclic amino(lower)alkyl esters include, e.g., N-pyrrolidinylmethyl, N-morpholinylethyl, N-methyl-3-morpholinylethyl, N-piperidinylethyl, N-ethyl-4-piperidinylethyl and the like.

Illustrative lower alkanoylamino(lower)alkyl esters include, e.g., acetamidoethyl, propionamidoethyl, succinimidoethyl and the like.

Suitable esters can also have the formulae I and II, wherein n=2–6, and $R_1$ is a lower alkyl or cyclo(lower-)alkyl polyol residue. Such esters include, e.g., di-, tri-, tetra-, penta- and hexaesters of an oxyoctadecanoic acid with an alkyl or cycloalkyl polyol, e.g., a $C_{1-6}$ alkylene glycol, glycerol, pentaerythritol, mannitol, inositol and the like.

The foregoing esters can generally be prepared by conventional esterification of the corresponding acids or by ester exchange with, e.g., the methyl ester. The acids of formulae I and II, wherein n=1 and $R_1$=H, can be prepared by adapting or following the preparative schemes disclosed in the Abbot et al. references mentioned hereinabove.

While facile syntheses of all possible stereoisomers of these compounds will not always be available, the highly sophisticated and versatile methods now available to the skilled art worker will permit the necessary functional group and stereochemical control and manipulation to provide any desired stereoisomer. For example, inversion of configuration of an alcohol may be effected by conversion to a good leaving group, e.g., a tosylate or mesylate, and $S_N2$ displacement by, e.g., acetate, followed by hydrolysis. Alcohols may also be oxidized to ketones and then selectively reduced to produce either or both stereoisomeric alcohols.

Alcohols can be dehydrated to produce the 10, 11 or 11,12 double bonds of compounds having the formulae I(f), I(h), II(c) and II(d). These olefinic compounds can be hydrated to form 10-ols, 11-ols and/or 12-ols by, e.g., hydroboration/oxidation, oxymercuration/demercuration, epoxidation/hydride reduction, or the like.

Ketones, e.g., compounds having the formulae I(b), I(d), I(g), I(h), II(b), II(d), II(f) and II(h), can be epimerized at the tertiary carbons adjacent to the ketone carbonyl groups to produce additional stereoisomers. The ketone carbonyls can later be reduced to alcohols or to methylene groups by conventional techniques.

Separation of stereoisomers and/or structural isomers will generally be effected by conventional techniques including, e.g., high performance liquid chromatography, thin layer and/or column chromatography, vapor phase chromatography, fractional crystallization and the like.

Pharmaceutically acceptable addition salts of the acids of formulae I and II, wherein n=1 and $R_1$=H, include inorganic or organic base addition salts which possess comparable psychotropic activity to the acid and which are otherwise physiologically compatible. Suitable inorganic bases to form these salts include, e.g., the hydroxides, carbonates, bicarbonates or alkoxides of the alkali metals or alkaline earth metals, e.g., sodium, potassium, magnesium, calcium and the like. Suitable organic bases include the following amines; lower mono-, di-, and trialkylamines, the alkyl radicals of which contain up to three carbon atoms, e.g., methylamine, dimethylamine, trimethylamine, ethylamine, di- and triethylamine, N-methyl-N-ethylamine, and the like; mono-, di- and trialkanolamines, the alkano radicals of which contain up to three carbon atoms, e.g., mono-, di- and triethanolamine, alkylenediamines which contain up to six carbon atoms, e.g., hexamethylenediamine; phenylalkylamines, e.g., benzylamine, phenylethylamine and N-methylphenylethylamine; cyclic saturated or unsaturated bases containing up to six carbon atoms, e.g., pyrrolidine, piperidine, morpholine, piperazine and their N-alkyl and N-hydroxyalkyl derivatives, e.g., N-methylmorpholine and N-(2-hydroxyethyl)-piperidine, as well as pyridine.

Furthermore, there may be mentioned the corresponding quaternary salts, e.g., the tetraalkyl, e.g., tetramethyl, alkylalkanol, e.g., methyltrimethanol and trimethylmonoethanol, and cyclic ammonium salts, e.g., the N-methylpyridinium, N-methyl-N-(2-hydroxyethyl)-morpholinium, N,N-dimethylmorpholinium, N-methyl-N-(2-hydroxyethyl)morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid in water containing at least one equivalent amount of a hydroxide, carbonate, or bicarbonate corresponding to the inorganic salt desired. Advantageously, the reaction is performed in a water-miscible, inert organic solvent for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, e.g., a lower alkanol, e.g., butanol, or a lower alkanone, e.g., ethyl methyl ketone, gives the solid inorganic salt if that form is desired.

To produce an amine salt, the acid is dissolved in a suitable solvent of either moderate or lower polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid with an equivalent amount of the corresponding quaternary ammonium hydroxide in water solution, followed by evaporation of the water.

Pharmaceutically acceptable addition salts also include salts of basic oxyoctadecanoate esters with physiologically compatible inorganic or organic acids. Such salts will generally possess comparable pharmacological activity to the corresponding esters, although it may be advantageous to administer the salts rather than the esters for some purposes. The acid addition salts are prepared by reacting a basic ester, e.g., a dialkylaminoalkyl oxyoctadecanoate or a cyclic aminoalkyl oxyoctadecanoate, with one or more equivalents, preferably with an excess, of the appropriate acid in an organic solvent, e.g., diethyl ether or an ethanol/diethyl ether mixture.

Suitable acids to form these salts include the common mineral acids, e.g., hydrohalic, sulfuric or phosphoric acid; as well as the organic acids, e.g., formic acetic, maleic, malic, ascorbic, succinic, fumaric, citric, or tartaric acid; or acids which are sparingly soluble in body fluids and which impart slow-release properties to their respective salts, e.g., pamoic or tannic acid or carboxymethylcellulose.

Also included in this invention are the stereoisomers of the compounds of formulae I and II which result from asymmetric centers contained therein. It is to be understood that the diastereomers arising from such asymmetry are included within the scope of this invention. Such diastereomers are obtained in substantially pure form by classical separation techniques and by sterically controlled synthesis.

Individual enantiomers, which might be separated by fractional crystallization of the diastereomeric salts thereof, are also included.

The foregoing examples of pharmaceutically acceptable esters and salts are intended to be illustrative of the scope of the invention, but not limitative thereof, and the invention includes equivalents of the illustrated compounds that also achieve the disclosed psychotropic response.

Illustrative examples of specific compounds which can be used in the method and composition of this invention include methyl 13-hydroxy-9,12-oxyoctadecanoate, tert-butyl 10-oxo-9,12-oxyoctadecanoate, pyridylmethyl 13-oxo-9,12-oxyoctadecanoate, sodium 9-hydroxy-10,13-oxyoctadecanoate, diethylaminoethyl 9,12-oxyoctadec-10-enoate, pyrrolidinoethyl 10,13-oxyoctadecanoate hydrochloride, 11-oxo-9,12-oxyoctadecanoic acid, ammonium 9-oxo-10,13-oxyoctadeconate, piperidinium 9-hydroxy-10,13-octadec-11-enoate, 1-morpholinoethyl 12-hydroxy-10,13-oxyoctadecanoate succinate, 1,2-propylene glycol bis(10,13-oxyoctadecanoate), pentaerythritol tetrakis(11-hydroxy-10,13-oxyoctadecanoate) and inositol hexakis(10,13-oxyoctadec-11-enoate). Preferred compounds are methyl 13-hydroxy-9,12-oxyoctadecanoate methyl 10-oxo-9,12-oxyoctadecanoate, methyl 13-oxo-9,12-oxyoctadecanoate, methyl 9-hydroxy-10,13-oxyoctadecanoate, methyl 9-oxo-10,13-oxyoctadecanoate, methyl 11-oxo-9,12-oxyoctadecanoate, the corresponding free acids and their sodium salts.

It will be appreciated that mixtures of the foregoing oxyoctadecanoates can also be employed in the method and composition of the invention.

Oxyoctadecanoates have now been found to possess psychotropic activity, i.e., administration of appropriate dosages to a human or animal subject elicits a psychotropic response. By psychotropic response is meant any one of a variety of therapeutic effects on the central nervous system, which include but are not limited to tranquilizing, antidepressant or anticonvulsant effects, as well as alleviation of the symptoms of alcohol intoxication and/or alcohol or tobacco withdrawal. A preferred method of use is in alleviating alcohol intoxication or withdrawal symptoms, wherein administration of an oxyoctadecanoate is particularly effective.

While the reasons for the effectiveness of any psychotropic agent are often unclear, it has been found that administration of an oxyoctadecanoate to humans and animals has a calming, anxiety-reducing effect which is especially helpful for those who are experiencing alcohol or tobacco withdrawal symptoms. In addition, other symptoms associated with alcohol withdrawal are reduced in severity upon administration of an effective amount of an oxyoctadecanoate in an appropriate dosage form.

Evaluation of the efficacy of oxyoctadecanoates in alleviating alcohol withdrawal symptoms is shown by the use of a reliable primate model system, wherein a Cynomolgus monkey is addicted to alcohol over a period of a few weeks, the alcohol is withdrawn and the presence and severity of specific symptoms associated with withdrawal are first evaluated during administration of a placebo, after which the animal is re-addicted to alcohol and the same symptoms are evaluated while an oxyoctadecanoate is administered during a withdrawal period of the same duration. A comparison of the total symptom score between the placebo withdrawal and the drug withdrawal period is a reliable measure of the efficacy of a drug in alleviating withdrawal symptoms, as disclosed in:

U.S. Ser. No. 106,129, filed Dec. 21, 1979. In that application, the primate model was used to evaluate a drug which was also clinically tested in a large number of subjects, and the primate model was shown to give results which were consistent with the clinical results.

Administration of an oxyoctadecanoate for the purpose of eliciting a psychotropic response is advantageously effected in daily amounts of about 0.1-150 mg per kg of patient body weight, preferably about 1-50 mg/kg. For the particular purpose of alleviating alcohol withdrawal symptoms, the daily dosage range is about 0.1-20 mg/kg, preferably about 0.5-10 mg/kg. The dose can be administered singly or as divided dosages throughout the day.

Administration of an oxyoctadecanoate in appropriate dosages to a human or animal, especially a mammal, suffering from nervousness and/or anxiety produces a calming, tranquilizing response. An effective daily tranquilizing dosage of an oxyoctadecanoate can generally range from about 10 mg to about 3 g, depending on the person or animal treated, the severity of the symptoms and the oxyoctadecanoate selected.

Administration of an oxyoctadecanoate in appropriate dosages to a human or animal, especially a mammal, suffering from convulsions produces an anticonvulsant response. An effective daily anticonvulsant dosage of an oxyoctadecanoate can generally range from about 10 mg to about 3 g, depending on the person or animal treated, the severity of the symptoms and the oxyoctadecanoate selected.

Administration of an oxyoctadecanoate in appropriate dosages to a human or animal, especially a mammal, suffering from depression produces an antidepressant response. An effective daily antidepressant dosage of an oxyoctadecanoate can generally range from about 10 mg to about 3 g, depending on the person or animal treated, the severity of the symptoms and the oxyoctadecanoate selected.

Administration of an oxyoctadecanoate in appropriate dosages to a human suffering from tobacco withdrawal symptoms alleviates the symptoms. An effective daily therapeutic dosage of an oxyoctadecanoate for alleviation of tobacco withdrawal symptoms can generally range from about 10 mg to about 3 g, depending on the person treated, the severity of the symptoms and the oxyoctadecanoate selected.

Oxyoctadecanoates may be provided in pure or substantially pure crystalline form for use in the method and composition of this invention. Alternatively, oxyoctadecanoates may be used in the form of mixtures of two or more enantiomers and/or diastereomers and/or isomers and/or structurally different oxyoctadecanoates of formulae I and/or II. It will often be convenient to use a mixture of products from a synthetic sequence, without separation of pure components, in the present method and composition.

While it appears that psychotropic activity is shown by substantially all of the compounds of formulae I and II, it may be found that certain of these compounds have modest or minimal activity. Nevertheless, the presence of such compounds in a mixture used in the present method and composition will generally not interfere with the activity of other active ingredients.

The compounds of this invention can be employed in mixture with conventional excipients, i.e., pharmaceutically acceptable organic or inorganic carrier substances suitable for parenteral or enteral application which do not deleteriously react with the active compounds. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, and the like. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or wheat starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, and the like.

Generally, the compounds of this invention are dispensed in unit dosage form comprising about 1 mg-1 g of a pharmaceutical carrier per each unit dosage and the amount of oxyoctadecanoate is about 0.5-1000 mg.

A preferred mode of administration is by oral administration of tablets and/or capsules containing an oxyoctadecanoate and one or more inert binders and/or excipients. The individual dosage units are advantageously tablets containing about 50-1000 mg of oxyoctadecanoate.

For a patient suffering from alcohol withdrawal symptoms, it is advantageous for the patient to take one such tablet four times per day for the first three days after withdrawal, desirably when the patient is sober, and to take one tablet two or three times per day for the next four days. Such a dosage of generally sufficient to eliminate or reduce the desire or need for alcohol and to alleviate any withdrawal symptoms which the patient might otherwise suffer. If the desire or need for alcohol recurs, the patient may be given an additional supply of the oxyoctadecanoate tablets, and directed to take a capsule if he or she feels any desire or need for alcohol or any recurrence of withdrawal symptoms.

A combination of injections and tablets or other oral dosage forms may also be used where indicated. In addition, the foregoing dosage forms may be used to reduce the severity of alcohol intoxication and/or to prevent or minimize alcohol intoxication prior to consumption of alcoholic beverages.

Similar dosage forms may be used for eliciting the broad range of psychotropic responses indicated hereinabove. The particular dosages will generally be within the broad ranges given above, but will vary in relation to the severity of the clinical symptoms and the type of response to be elicited, in a manner which will be familiar to the skilled clinical practitioner.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Tablet Formulation

A tablet suitable for administration according to the method of the invention is prepared as follows. Each dosage unit is designed for administration to a patient weighing about 80 kg, and administration of four such tablets on each of the first three days of alcohol withdrawal and two or three tablets for each of the next four days is envisioned. Suitable variation and dosage as a function of patient weight is indicated.

|  |  | Weight |
|---|---|---|
| (a) | Methyl 13-hydroxy-9,12-oxyoctadecanoate | 200 g |
| (b) | Wheat starch | 26 g |
| (c) | Lactose | 76 g |
| (d) | Magnesium stearate | 6 g |

A granulation obtained upon mixing lactose with a portion of the starch and granulated starch paste made from the remainder of the starch is dried, screened and mixed with the oxyoctadecanoate and the magnesium stearate. The mixture is compressed into 1,000 tablets weighing about 308 mg each. It will be understood that a dragee or a capsule may be used in place of a tablet, and it may be prepared by conventional techniques.

EXAMPLE 2

Two different oxyoctadecanoates were tested for their efficacy in alleviating alcohol withdrawal symptoms in an alcohol-addicted Cynomolgus monkey, using water as a placebo. For each test, a monkey was addicted to ethyl alcohol by infusion of 5 ml/hr for 28 days of a solution ranging between 15 and 30% ethyl alcohol in normal saline. The ethyl alcohol solution was administered via an indwelling silastic catheter implanted into the jugular vein. The presence of and severity of withdrawal was evaluated according to the presence and severity of specific symptoms, which are known to be exhibited by monkeys upon removal of alcohol in a dependent animal. Evaluation was based on a scale of 0: symptom not present, 1: mild presence of symptom, 2: moderate presence of symptom, and 3: severe presence of symptom. The symptoms evaluated were: generalized tremors, muscle fasciculations, elicited hyperreflexia, spasticity, rigidity, spontaneous hyperreflexia, fright, salivation, mydriasis, retching-vomiting, convulsive poses, convulsions, aggression, nervousness, excitability, and evoked threat.

During the 5-day placebo withdrawal period, which immediately followed the 28-day addiction period, the monkey received 5 ml of water injected into orange slices. The withdrawal symptoms were evaluated daily during this period. At the conclusion of the placebo withdrawal period, the animal was re-addicted to the ethyl alcohol over a 14-day period as described above. This was immediately followed by a 5-day drug withdrawal period. During this period, the animal received a daily dose of 17.9 mg of the oxyoctadecanoate dissolved in 5 ml of triolein and injected into orange slices, and the daily withdrawal symptoms were each evaluated using the above rating system. The lower the score, the less severe the symptoms and the more efficacious the therapeutic effect compared to placebo administration. In each test run, the total symptom scores for placebo and for the oxyoctadecanoate were determined, and the reduction (placebo-drug/placebo × 100) for each test was calculated. A percent reduction higher than 20% is considered significant. The results are shown in the Table.

TABLE

| Run | oxyoctadecanoate tested | Placebo | Drug | Reduction |
|---|---|---|---|---|
| 1 | Methyl-13-hydroxy-9,12-oxyoctadecanoate | 46 | 17 | 63% |
| 2 | Methyl-13-hydroxy-9,12-oxyoctadecanoate | 47 | 30 | 36% |
| 3 | Methyl 10-oxo-9,12-oxyoctadecanoate | 50 | 10 | 80% |

It can be seen from these data that oxyoctadecanoates have been shown to be effective for alleviation of the symptoms of alcohol withdrawal in a reliable primate model. Oxyoctadecanoates were most effective in reducing nervousness, aggression, fright, threat and generalized tremors.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions. Contemplated modifications include mono or poly substitution of moieties on the oxyoctadecanoate acid that will not interfere with its psychotropic activity, either as such or in its ester and/or salt forms. Suitable such substituents would include halogen atoms, lower alkyl, lower alkoxy, hydroxy and the like, which can be introduced by conventional means.

What is claimed is:

1. A method for producing a psychotropic response in a human or animal subject suffering from a condition for which a psychotropic response would be therapeutic, comprising administering to said subject a psychotropically effective non-toxic amount of a 9,12-oxyoctadecanoate having the formula I

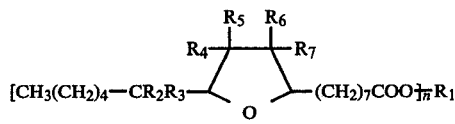

wherein n=1 and $R_1$ is H, lower alkyl, cyclo(lower)alkyl, aryl(lower)alkyl, lower alkoxy(lower)alkyl, di(lower)alkylamino(lower)alkyl, cyclic amino(lower)alkyl or alkanoylamino(lower)alkyl; or n=2-6 and $R_1$ is a lower alkyl or cyclo(lower)alkyl polyol residue; and (a) $R_2$, $R_3$, $R_4$, $R_5$ and $R_6$ are each H; and $R_7$ is OH; or
(b) $R_2$, $R_3$, $R_4$ and $R_5$ are each H; and $R_6$ and $R_7$ together are O; or
(c) $R_2$, $R_3$, $R_4$, $R_6$ and $R_7$ are each H; and $R_5$ is OH; or
(d) $R_2$, $R_3$, $R_6$ and $R_7$ are each H; and $R_4$ and $R_5$ together are O; or
(e) $R_2$ is OH; and $R_3$, $R_4$, $R_5$, $R_6$ and $R_7$ are each H; or
(f) $R_2$ is OH; $R_3$, $R_4$ and $R_6$ are each H; and $R_5$ and $R_7$ together are a C—C bond; or
(g) $R_2$ and $R_3$ together are O; and $R_4$, $R_5$, $R_6$ and $R_7$ are each H; or
(h) $R_2$ and $R_3$ together are O; $R_4$ and $R_6$ are each H; and $R_5$ and $R_7$ together are a C—C bond; or a 10,13-oxyoctadecanoate having the formula II

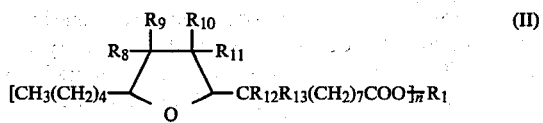

wherein n and $R_1$ are as defined hereinabove; and (a) $R_8$, $R_9$, $R_{10}$, $R_{11}$ and $R_{12}$ are each H; and $R_{13}$ is OH; or
(b) $R_8$, $R_9$, $R_{10}$ and $R_{11}$ are each H; and $R_{12}$ and $R_{13}$ together are O; or
(c) $R_8$, $R_{10}$ and $R_{12}$ are each H; $R_9$ and $R_{11}$ together are a C—C bond; and $R_{13}$ is OH; or
(d) $R_8$ and $R_{10}$ are each H; $R_9$ and $R_{11}$ together are a C—C bond; and $R_{12}$ and $R_{13}$ together are O; or
(e) $R_8$, $R_9$, $R_{10}$, $R_{12}$ and $R_{13}$ are each H; and $R_{11}$ is OH; or
(f) $R_8$, $R_9$, $R_{12}$ and $R_{13}$ are each H; and $R_{10}$ and $R_{11}$ together are O; or
(g) $R_8$ is OH; and $R_9$, $R_{10}$, $R_{11}$, $R_{12}$, and $R_{13}$ are each H; or
(h) $R_8$ and $R_9$ together are O; and $R_{10}$, $R_{11}$, $R_{12}$ and $R_{13}$ are each H; or a pharmaceutically acceptable addition salt thereof.

2. The method of claim 1, wherein said subject is suffering from symptoms of alcohol withdrawal and said response is alleviation of alcohol withdrawal symptoms.

3. The method of claim 1, wherein said subject is suffering from anxiety and said response is a tranquilizing effect.

4. The method of claim 1, wherein said subject is suffering from depression and said response is an antidepressant effect.

5. The method of claim 1, wherein said subject is suffering from convulsions and said response is an anticonvulsant effect.

6. The method of claim 1, wherein said subject is suffering from symptoms of alcohol intoxication and said response is alleviation of the symptoms of alcohol intoxication.

7. The method of claim 1, wherein said subject is suffering from symptoms of tobacco withdrawal and said response is alleviation of tobacco withdrawal symptoms.

8. The method of claim 1, wherein said effective amount is about 0.1-150 mg per kg of subject body weight per day.

9. The method of claim 8, wherein said amount is about 1-50 mg/kg/day.

10. The method of claim 1, wherein the oxyoctadecanoate is administered orally.

11. The method of claim 2, wherein said effective amount is about 0.1–20 mg per kg of subject body weight per day.

12. The method of claim 11, wherein said amount is about $0.5 \propto 10$ mg/kg.

13. The method of claim 11, wherein the oxyoctadecanoate is administered orally.

14. The method of claim 1, wherein the oxyoctadecanoate is methyl 13-hydroxy-9,12-oxyoctadecanoate, methyl 10-oxo-9,12-oxyoctadecanoate, methyl 13-oxo-9,12-oxyoctadecanoate, methyl 9-hydroxy-10,13-oxyoctadecanoate, methyl 9-oxo-10,13-oxyoctadecanoate, methyl 11-oxo-9,12-oxyoctadecanoate, the corresponding free acids and their sodium salts.

15. The method of claim 2, wherein the oxyoctadecanoate is methyl 13-hydroxy-9,12-oxyoctadecanoate, methyl 10-oxo-9,12-oxyoctadecanoate, methyl 13-oxo-9,12-oxyoctadecanoate, methyl 9-hydroxy-10,13-oxyoctadecanoate, methyl 9-oxo-10,13-oxyoctadecanoate, methyl 9-oxo-10,13-oxyoctadecanoate, methyl 11-oxo-9,12-oxyoctadecanoate, the corresponding free acids and their sodium salts.

16. The method of claim 15, wherein the oxyoctadecanoate is methyl 3-hydroxy-9,12-oxyoctadecanoate or methyl 10-oxo-9,12-oxyoctadecanoate.

17. A psychotropic composition, consisting essentially of (1) a non-toxic amount effective for producing a psychotropic response in a human or animal subject of a 9,12-oxyoctadecanoate having the formula I

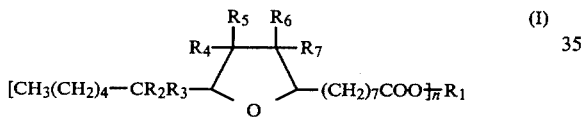

wherein $n=1$ and $R_1$ is H, lower alkyl, cyclo(lower)alkyl, aryl(lower)alkyl, lower alkoxy(lower)alkyl, di(lower)alkylamino(lower)alkyl, cyclic amino(lower)alkyl or alkanoylamino(lower)alkyl; or $n=2–6$ and $R_1$ is a lower alkyl or cyclo(lower)alkyl polyol residue; and (a) $R_2$, $R_3$, $R_4$, $R_5$ and $R_6$ are each H; and $R_7$ is OH; or (b) $R_2$, $R_3$, $R_4$ and $R_5$ are each H; and $R_6$ and $R_7$ together are O; or (c) $R_2$, $R_3$, $R_4$, $R_6$ and $R_7$ are each H; and $R_5$ is OH; or (d) $R_2$, $R_3$, $R_6$ and $R_7$ are each H; and $R_4$ and $R_5$ together are O; or (e) $R_2$ is OH; and $R_3$, $R_4$, $R_5$, $R_6$ and $R_7$ are each H; or (f) $R_2$ is OH; $R_3$, $R_4$ and $R_6$ are each H; and $R_5$ and $R_7$ together are a C—C bond; or (g) $R_2$ and $R_3$ together are O; and $R_4$, $R_5$, $R_6$ and $R_7$ are each H; or (h) $R_2$ and $R_3$ together are O; $R_4$ and $R_6$ are each H; and $R_5$ and $R_7$ together are a C—C bond; or a 10,13-oxyoctadecanoate having the formula II

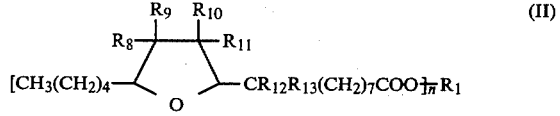

wherein n and $R_1$ are as defined hereinabove; and (a) $R_8$, $R_9$, $R_{10}$, $R_{11}$ and $R_{12}$ are each H; and $R_{13}$ is OH; or (b) $R_8$, $R_9$, $R_{10}$ and $R_{11}$ are each H; and $R_{12}$ and $R_{13}$ together are O; or (c) $R_8$, $R_{10}$ and $R_{12}$ are each H; $R_9$ and $R_{11}$ together are a C—C bond; and $R_{13}$ is OH; or (d) $R_8$ and $R_{10}$ are each H; $R_9$ and $R_{11}$ together are a C—C bond; and $R_{12}$ and $R_{13}$ together are O; or (e) $R_8$, $R_9$, $R_{10}$, $R_{12}$ and $R_{13}$ are each H; and $R_{11}$ is OH; or (f) $R_8$, $R_9$, $R_{12}$ and $R_{13}$ are each H; and $R_{10}$ and $R_{11}$ together are O; or (g) $R_8$ is OH; and $R_9$, $R_{10}$, $R_{11}$, $R_{12}$, and $R_{13}$ are each H; or (h) $R_8$ and $R_9$ together are O; and $R_{10}$, $R_{11}$, $R_{12}$ and $R_{13}$ are each H; or a pharmaceutically acceptable addition salt thereof;

and (2) a pharmaceutically acceptable carrier; wherein said composition is in unit dosage form as a tablet, dragee, capsule, ampoule, suppository or sterile injectable preparation.

18. The composition of claim 17, wherein the oxyoctadecanoate is methyl 13-hydroxy-9,12-oxyoctadecanoate, methyl 10-oxo-9,12-oxyoctadecanoate, methyl 13-oxo-9,12-oxyoctadecanoate, methyl 9-hydroxy-10,13-oxyoctadecanoate, methyl 9-oxo-10,13-oxyoctadecanoate, methyl 11-oxo-9,12-oxyoctadecanoate, the corresponding free acids and their sodium salts.

19. The composition of claim 17, wherein the oxyoctadecanoate is methyl 13-hydroxy-9,12-oxyoctadecanoate or methyl 10-oxo-9,12-oxyoctadecanoate.

* * * * *